(12) United States Patent
Wang et al.

(10) Patent No.: US 8,923,480 B2
(45) Date of Patent: Dec. 30, 2014

(54) X-RAY DIFFRACTION INSTRUMENT

(75) Inventors: Yun Wang, Hitachi (JP); Hisamitu Hatou, Hitachi (JP); Toshikazu Kikuchi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 324 days.

(21) Appl. No.: 13/570,453

(22) Filed: Aug. 9, 2012

(65) Prior Publication Data
US 2013/0044864 A1    Feb. 21, 2013

(30) Foreign Application Priority Data
Aug. 18, 2011    (JP) ................. 2011-178976

(51) Int. Cl.
*G01N 23/20* (2006.01)
*G01L 5/00* (2006.01)
*G01L 1/25* (2006.01)

(52) U.S. Cl.
CPC ...... *G01N 23/20008* (2013.01); *G01N 2223/62* (2013.01); *G01L 5/0047* (2013.01); *G01L 1/25* (2013.01)
USPC .......................................................... 378/71

(58) Field of Classification Search
CPC ... G01N 23/207; G01N 23/20; G01N 23/205; A61B 6/107; H01J 35/16; H05G 1/04
USPC ............................................. 378/71–81, 203
See application file for complete search history.

(56) References Cited

U.S. PATENT DOCUMENTS

| 2,259,708 A | 10/1941 | Schiebold |
| 2,462,374 A | 2/1949 | Firth |
| 4,042,825 A | 8/1977 | Ruud |
| 4,263,510 A * | 4/1981 | Ciccarelli et al. ............... 378/46 |
| 5,741,707 A | 4/1998 | Herron et al. |
| 6,285,736 B1 | 9/2001 | Dosho |
| 6,353,656 B1 | 3/2002 | LeVert et al. |
| 2012/0140888 A1 | 6/2012 | Wang |

FOREIGN PATENT DOCUMENTS

| JP | 6-317484 A | 11/1994 |
| JP | 2000-146871 A | 5/2000 |
| JP | 2005-241308 A | 9/2005 |
| JP | 2005-351780 A | 12/2005 |
| JP | 2012-122737 A | 6/2012 |

OTHER PUBLICATIONS

Partial European Search Report Dated Jun. 5, 2013 (Eight (8) pages).

* cited by examiner

*Primary Examiner* — Courtney Thomas
(74) *Attorney, Agent, or Firm* — Crowell & Moring LLP (57) ABSTRACT

There is provided an X-ray diffraction instrument including: a two-dimensional plate-like X-ray detector; an X-ray emitter integrated with the X-ray detector so as to penetrate the plate of the X-ray detector; a cylinder-like shield to define an orientation of the X-ray emitter and to prevent X-ray leakage, the X-ray detector being attached to one open end of the cylinder-like shield; and a standard powder attachment device to attach a standard powder for X-ray diffraction measurement to a surface of an object to be measured. The X-ray diffraction instrument can perform an X-ray diffraction measurement to an object larger than the X-ray detector thereof. The invented X-ray diffraction instrument is small in size, and can perform accurate X-ray diffraction measurement of stationary immovable objects without limitation on an orientation of the measurement surface. In addition, X-ray leakage is prevented for operator safety.

15 Claims, 7 Drawing Sheets

X-RAY DIFFRACTION INSTRUMENT

CLAIM OF PRIORITY

The present application claims priority from Japanese patent application serial no. 2011-178976 filed on Aug. 18, 2011, the content of which is hereby incorporated by reference into this application.

BACKGROUND OF THE INVENTION

1. Field of the Invention

The present invention relates to X-ray diffraction instruments, and particularly to X-ray diffraction instruments for detecting X-ray diffraction patterns two-dimensionally and estimating residual stresses of measurement objects.

2. Description of Related Art

X-ray diffraction instruments are used as a non-destructive inspection tool for measuring various material properties (such as crystallographic structure, composition and residual stress). Goniometers, zero-dimensional scintillation counters (SC), one-dimensional position sensitive detectors (PSD), etc. are commonly and widely used to obtain X-ray diffraction data (such as intensity and angle of diffraction). However, these instruments offer only zero-/one-dimensional diffraction data by a single measurement. Thus, a complicated actuator and a long total measurement time are needed to obtain sufficient diffraction data required for a thoroughly satisfactory material analysis.

To overcome this disadvantage, X-ray diffraction instruments including a two-dimensional X-ray detector which provide a larger amount of diffraction information in a shorter period of measurement time are used. Examples of two-dimensional X-ray detectors include two-dimensional position sensitive proportional counters (PSPC) and imaging plates (IP). Imaging plates are a type of ionizing radiation image detector in which a photostimulable phosphor such as BaFX:$Eu^{2+}$ (X=Br, I) is applied on a support plate made of a plastic or the like.

JP-A 2000-146871 discloses a micro X-ray diffraction instrument and a method of measurement, in which a micro area of a specimen is irradiated with an X-ray beam and the X-ray beams diffracted by the specimen are detected by a two-dimensional X-ray detector. The two-dimensional X-ray detector used in this micro X-ray diffraction instrument is a cylinder made of a photostimulable phosphor, and is placed in such a manner as to surround the specimen. The specimen is tilted (e.g., by 45°) so that both the X-ray beams diffracted in directions tangential to the specimen surface and the X-ray beams diffracted in directions normal to the specimen surface can be detected by the photostimulable phosphor X-ray detector. By using the JP-A 2000-146871 X-ray diffraction instrument, sufficient X-ray diffraction data can be captured by the photostimulable phosphor detector by rotating the specimen around only one axis (normal to the specimen surface), which is advantageous over most conventional X-ray diffraction instruments requiring rotations about two axes. Thus, this X-ray diffraction instrument has the advantage of simple structure, high diffraction intensity and short total measurement time.

JP-A 2005-351780 discloses an X-ray diffraction instrument including a two-dimensional X-ray detector that provides transmission diffraction measurement. This X-ray diffraction instrument includes: a specimen table for horizontally holding a specimen; an X-ray emitter for irradiating the specimen with an X-ray beam; an arm for actuating the X-ray emitter in such a way that the incident angle of the emitted X-ray beam relative to the specimen is set at a desired angle from 0° to 90°; and a partially-open cylinder made of a storage (photostimulable) phosphor that surrounds the specimen table for detecting the X-ray beams diffracted by the specimen. The phosphor cylinder is placed in such a manner that its axis is perpendicular to the emitted X-ray beam. The phosphor detector portion of the cylinder barrel extends circumferentially from 180° to 360° as measured from the horizontal (parallel to the table surface) on the side of the X-ray emitter, and more preferably from 100° to 360°, and the other portion of the cylinder barrel is open. The JP-A 2005-351780 X-ray diffraction instrument provides transmission diffraction measurement as well as reflection diffraction measurement.

JP-A Hei 6 (1994)-317484 discloses an X-ray exposure system for micro-area stress measurement including (from upstream to downstream along the X-ray path): a slit and first (upstream) screen; a sample stage mounted on a rotatable goniometer; an imaging plate on a support that is mounted on an arm rotatable about the emitted X-ray axis; and a second (downstream) screen just in front of the imaging plate. The emitted X-ray beam passes through the slit and first screen and is incident on a micro-area (e.g., 100 µm to 1 mm square) of a sample, and several discrete X-ray diffraction arcs (each being a part of a Debye ring) obtained by changing the X-ray angle incident on the sample several times are exposed on the same single stationary imaging plate. According to this JP-A Hei 6 (1994)-317484, several discrete X-ray arcs can be detected by a single measurement with a high angular accuracy, thus enabling micro-area stress measurement of polycrystalline materials in a short period of time.

JP-A 2005-241308 discloses an X-ray diffraction system in which a measurement object (a railway rail) is irradiated with X-ray and an image of the X-ray diffraction ring from the measurement object is captured. This X-ray system includes: an X-ray emitter for emitting the X-ray and an X-ray detector for storing the energy of the X-ray diffraction ring and producing the image of the diffraction ring. The X-ray emitter and the X-ray detector are mounted on a holder in such a manner the X-ray incident angle relative to the measurement object is fixed at a single angle. According to this JP-A 2005-241308, the X-ray diffraction system can perform X-ray diffraction measurement simply and conveniently. Also, the system is easy to use, cheap to manufacture and portable. In addition, the physical condition (such as residual stress) of a measurement object (a railway rail) can be evaluated by comparing the diffraction rings of the measurement object and of a standard specimen (an iron standard powder).

However, the X-ray diffraction instruments of JP-A 2000-146871 and JP-A 2005-351780 require an actuator for adjusting the position and/or orientation of the specimen and/or the X-ray emitter, and thus have disadvantages of complicated structure and large size. In addition, the two-dimensional X-ray detectors used in the above disclosures are cylindrical in form, and surround a specimen for detecting the X-ray beams diffracted by the specimen. Therefore, there is some limitation on the size and shape of specimens measurable by these X-ray diffraction instruments. In general, specimens measurable by conventional X-ray diffraction instruments are limited to relatively small objects (such as laboratory samples).

Also, the X-ray exposure system for micro-area stress measurement of JP-A Hei 6 (1994)-317484 requires a goniometer for rotating a sample stage on which a specimen is mounted, and thus has a disadvantage of complicated structure and some limitation on the size and shape of specimens to be measured. Furthermore, JP-A Hei 6 (1994)-317484 describes that, in order to measure the micro-area stress of the measurement specimen, a standard powder is placed on the specimen and that the X-ray is irradiated to both the specimen and the standard powder at the same time. However, JP-A Hei 6 (1994)-317484 is silent to a fixing method of the standard powder to the specimen.

Recently, there has been an increasing demand for on-site non-destructive inspection of the conditions (such as material abnormality and deterioration) of structural components of large apparatuses used in various plants. As described in JP-A 2000-146871, JP-A 2005-351780 and JP-A Hei 6 (1994)-317484, most conventional X-ray diffraction instruments are large in size, and there is some limitation on the size and shape of specimens. Thus, conventional X-ray instruments are very difficult to use as a tool for inspecting structural components of large apparatuses both non-destructively and on-site.

The X-ray diffraction system of JP-A 2005-241308 has advantages in that the X-ray emitter can stably impinge X-ray on a large measurement object at a predetermined fixed incident angle, and any actuator for rotating the measurement object is not required. However, JP-A 2005-241308 does not describe any method for setting the standard specimen required for the residual stress measurement. This is probably because the JP-A 2005-241308 technology is practically limited to the top surface of a railway rail. Also, this disclosure does not describe any measure to prevent leakage of X-ray emitted from the X-ray emitter or scattered by the measurement object.

When X-ray diffraction measurement of large apparatuses in plants or other systems is performed on-site, the measurement surfaces (the surfaces to be measured) may often be vertical or face downward. In such cases, it is difficult to stably attach a standard powder on a measurement surface, thus making accurate measurement and estimation difficult. Also, contamination by foreign materials is unacceptable in some plants. In such environments, attaching a standard powder on a measurement surface without scattering the powder is a particularly important requirement. In addition, it is desirable for operator safety to prevent X-ray leakage.

SUMMARY OF THE INVENTION

In order to address the above problems and requirements, it is an objective of the present invention to provide an X-ray diffraction instrument without any actuator for adjusting the position and/or orientation of a measurement object, in which: there is no particular limitation on the size and shape of the measurement object; a standard powder can be stably attached on the surface of the measurement object; and X-ray leakage is prevented.

According to an aspect of the present invention, there is provided an X-ray diffraction instrument including:

a two-dimensional plate-like X-ray detector;

an X-ray emitter integrated with the X-ray detector so as to penetrate the plate of the X-ray detector;

a cylinder-like shield to define an orientation of the X-ray emitter and to prevent X-ray leakage, the X-ray detector being attached to one open end of the cylinder-like shield; and a standard powder attachment device to attach a standard powder for X-ray diffraction measurement to a surface of an object to be measured. The X-ray diffraction instrument can perform an X-ray diffraction measurement to an object larger than the X-ray detector thereof.

In the above aspect of the present invention, the following modifications and changes can be made.

i) The standard powder attachment device is an injector to inject a dispersion of the standard powder in a dispersion medium; and the injector is integrated with the X-ray detector so as to penetrate the X-ray detector.

ii) The standard powder attachment device is a polymer sheet having the standard powder dispersed therein; and the polymer sheet covers the other open end of the cylinder-like shield facing a surface of the object to be measured. The polymer sheet is attached to the object surface by pushing the polymer sheet against the object surface to be measured.

iii) A thickness of the polymer sheet is from 0.1 to 0.5 mm.

iv) The cylinder-like shield is detachable and easily exchangeable for another cylinder-like shield.

v) The X-ray emitter includes a sighting device.

vi) The X-ray detector is an imaging plate including a photostimulable phosphor layer.

vii) The cylinder-like shield blocks visible light.

viii) The imaging plate is housed in a cartridge that transmits X-ray but blocks visible light.

ix) The imaging plate is detachable and easily exchangeable for another imaging plate.

x) The X-ray detector is a position-sensitive proportional counter.

Advantages of the Invention

According to the present invention, it is possible to provide an X-ray diffraction instrument without any actuator for adjusting the position and/or orientation of a measurement object, in which there is no particular limitation on the size and shape of the measurement object and a standard powder can be stably attached on a surface of the measurement object. The invented X-ray diffraction instrument is small in size, and can perform accurate X-ray diffraction measurement of stationary immovable objects (e.g., on-site inspection of structural components of large apparatuses) without limitation on an orientation of the measurement surface. In addition, X-ray leakage is prevented for operator safety.

DETAILED DESCRIPTION OF THE PREFERRED EMBODIMENTS

Preferred embodiments of the present invention will be described below with reference to the accompanying drawings. In the drawings, like parts are designated by like reference numerals without repeating the description thereof. The invention is not limited to the specific embodiments described below, but various combinations and modifications are possible without departing from the spirit and scope of the invention.

Figure 1:
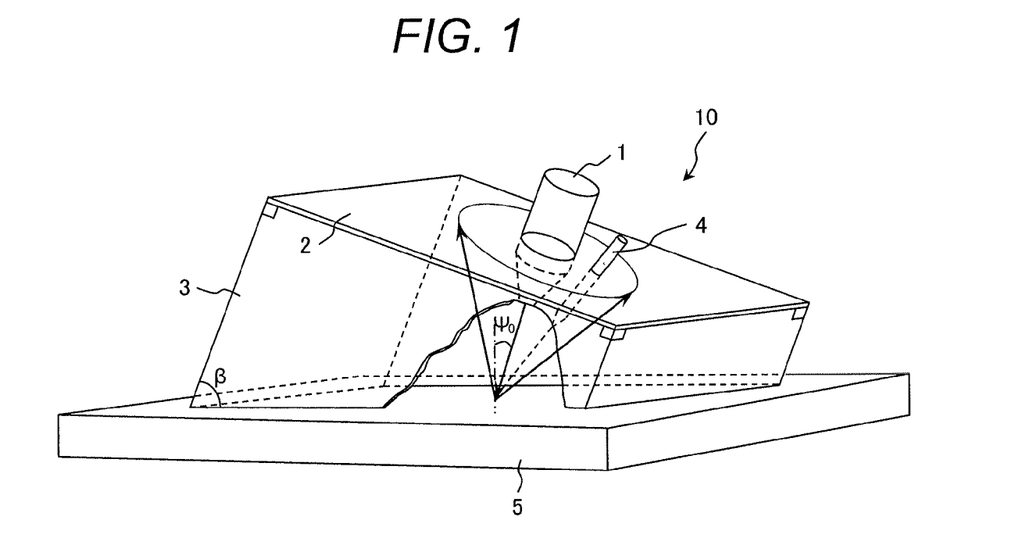
FIG. 1 is a schematic illustration showing a perspective view of an embodiment of an X-ray diffraction instrument according to the present invention.

FIG. 1 is a schematic illustration showing a perspective view of an embodiment of an X-ray diffraction instrument according to the present invention. As illustrated, an X-ray diffraction instrument 10 of the present invention includes: a two-dimensional plate-like X-ray detector 2; an X-ray emitter 1 integrated with the X-ray detector 2 so as to penetrate the plate of the X-ray detector 2; and a cylinder-like shield 3 to define an orientation of the X-ray emitter 1 and to prevent X-ray leakage. The X-ray detector 2 is attached to one open end of the cylinder-like shield 3 in such a manner that the perimeter of the open end of the cylinder-like shield 3 abuts the perimeter of the detector 2. As illustrated in FIG. 1, the X-ray diffraction instrument 10 can perform an X-ray diffraction measurement to a measurement object 5 whose size is larger than the X-ray detector 2. The X-ray diffraction instrument 10 further includes, as a standard powder attachment device to attach a standard powder for X-ray diffraction measurement to a surface of the measurement object 5, an injector 4 to inject a dispersion of the standard powder in a dispersion medium.

An X-ray beam emitted from the X-ray emitter 1 (e.g., X-ray tube) is incident on and diffracted by the measurement object 5, and then the diffracted X-ray beams are incident on and detected by the X-ray detector 2 where the diffraction pattern of the measurement object 5 is recorded. Herein, the X-ray beams (the emitted X-ray beam and the diffracted X-ray beams) are surrounded and blocked by the cylinder-like shield 3. Thus, the above diffraction measurement can be carried out safely without any X-ray leakage. Preferably, the X-ray emitter 1 is equipped with an unshown sighting device (such as a laser pointer) for visibly showing a point on the measurement object 5 to be irradiated with the emitted X-ray beam. By using this sighting device, the X-ray diffraction instrument 10 can be easily positioned in such a manner that the X-ray emitter 1 emits an X-ray beam onto an exactly desired target area on the measurement object 5.

The X-ray emitter 1 is integrally and immovably fixed to the X-ray detector 2. An angle between the emitting axis of the X-ray emitter 1 and the plane of the X-ray detector 2 may be freely chosen depending on a surface contour of the measurement object 5, a type of X-ray diffraction analysis or other factors. However, the angle is preferably 90° because of the effective use of the X-ray receiving surface of the X-ray detector 2 and the analytical ease of the resulting diffraction pattern.

Also, a position of the X-ray emitter 1 in the plane of the X-ray detector 2 is not particularly limited, but may be freely chosen depending on a type of X-ray diffraction analysis. For example, when the entire circumferences of a relatively small number of Debye rings needs to be recorded, the X-ray emitter 1 is preferably located near the center of the plane of the X-ray detector 2. When the partial circumferences of relatively many Debye rings needs to be recorded, the X-ray emitter 1 is preferably located near a side edge of the plane of the X-ray detector 2.

The cylinder-like (tube) shield 3 defines an orientation of the X-ray emitter 1 as well as providing X-ray blocking. When the X-ray emitter 1 is perpendicularly fixed to the X-ray detector 2, an incident angle $\Psi$ of the emitted X-ray beam (relative to the normal to the surface of the measurement object 5) and a tilt angle $\beta$ of the cylinder-like shield 3 (relative to the surface of the measurement object 5) satisfy a relationship of "$\Psi=90°-\beta$" (see FIG. 1). Thus, the incident angle can be changed by using a cylinder-like shield 3 having a different tilt angle $\beta$. In order to readily change the incident angle by exchange of the cylinder-like shield 3, the X-ray detector 2 is preferably detachably attached to the cylinder-like shield 3 when the X-ray emitter 1 is immovably fixed to the X-ray detector 2.

Preferably, the injector 4 is integrated with the X-ray detector 2 so as to penetrate the X-ray detector 2 in order to achieve stable injection of the standard powder dispersion and not to block the incident and diffracted X-ray beams. For example, it is desirable that the injector 4 is located within the smallest Debye ring on the X-ray detector 2.

Figure 2:
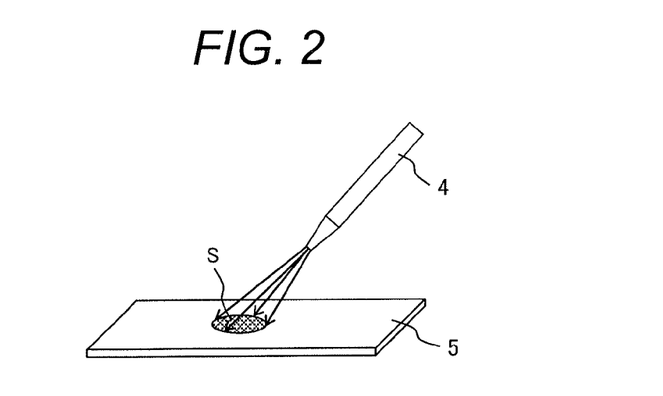
FIG. 2 is a schematic illustration showing a perspective view of an example of an injector used in the invented X-ray diffraction instrument.

FIG. 2 is a schematic illustration showing a perspective view of an example of an injector used in the invented X-ray diffraction instrument. In this figure, parts other than the injector 4 and the measurement object 5 are not illustrated for simplicity of illustration. As illustrated, the injector 4 is used to inject a dispersion of a standard powder for X-ray measurement onto a target measurement surface of the measurement object 5. By drying the standard powder dispersion on the measurement object 5, a standard powder coating S can be adhesively formed on the measurement surface of the measurement object 5. In this way, an X-ray measurement standard powder can be adhesively disposed on a measurement surface even when the measurement surface is vertical or faces downward. Thus, X-ray measurement of the standard powder can be stably performed. After the X-ray measurement, the standard powder coating S is removed by wiping. There is no particular limitation on the injector 4, but, for example, an air brush may be used.

The above-mentioned standard powder is used to investigate the properties (such as residual stress) of the measurement object 5 by X-ray diffraction measurement. Typically, a crystalline powder whose internal strain is completely or sufficiently relaxed is used. The dispersion medium is preferably alcohol and/or water in order to readily dry the deposited standard powder dispersion. An organic binder or the like may be added to the standard powder dispersion to facilitate the formation of the standard powder coating S.

A volume ratio of the standard powder to the dispersion medium (volume of standard powder)/(volume of dispersion medium) is preferably from 0.5 to 5. When the volume ratio is less than 0.5, the X-ray diffraction intensity from the standard powder is not sufficiently strong or the deposited standard powder dispersion is prone to drip off the surface of the measurement object 5. On the other hand, volume ratios higher than 5 reduce the fluidity of the standard powder dispersion and the adhesiveness of the standard powder coating S (and, as a result, the standard powder coating S is prone to partially peel and drop from the measurement object 5.)

Figure 3:
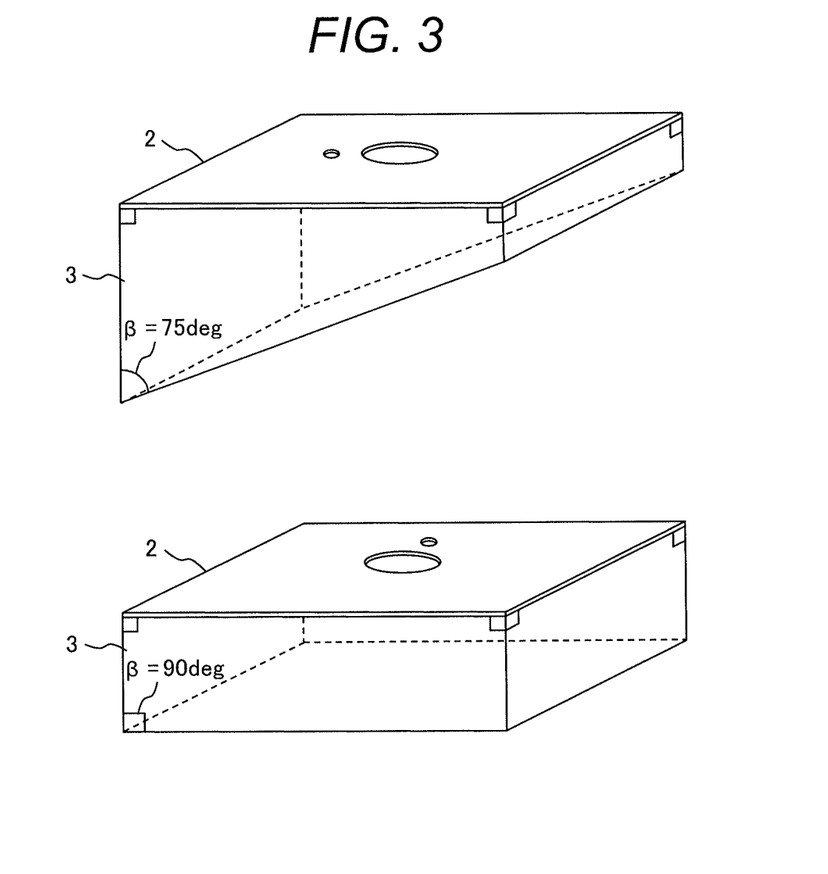
FIG. 3 is a schematic illustration showing perspective views of cylinder-like shields having different tilt angles βs.

FIG. 3 is a schematic illustration showing perspective views of cylinder-like shields having different tilt angles βs. As illustrated in FIG. 3, the incident angle Ψ can be set at 25° and 0° by using cylinder-like shields 3 having tilt angles β of 75° and 90°, respectively.

Figure 4:
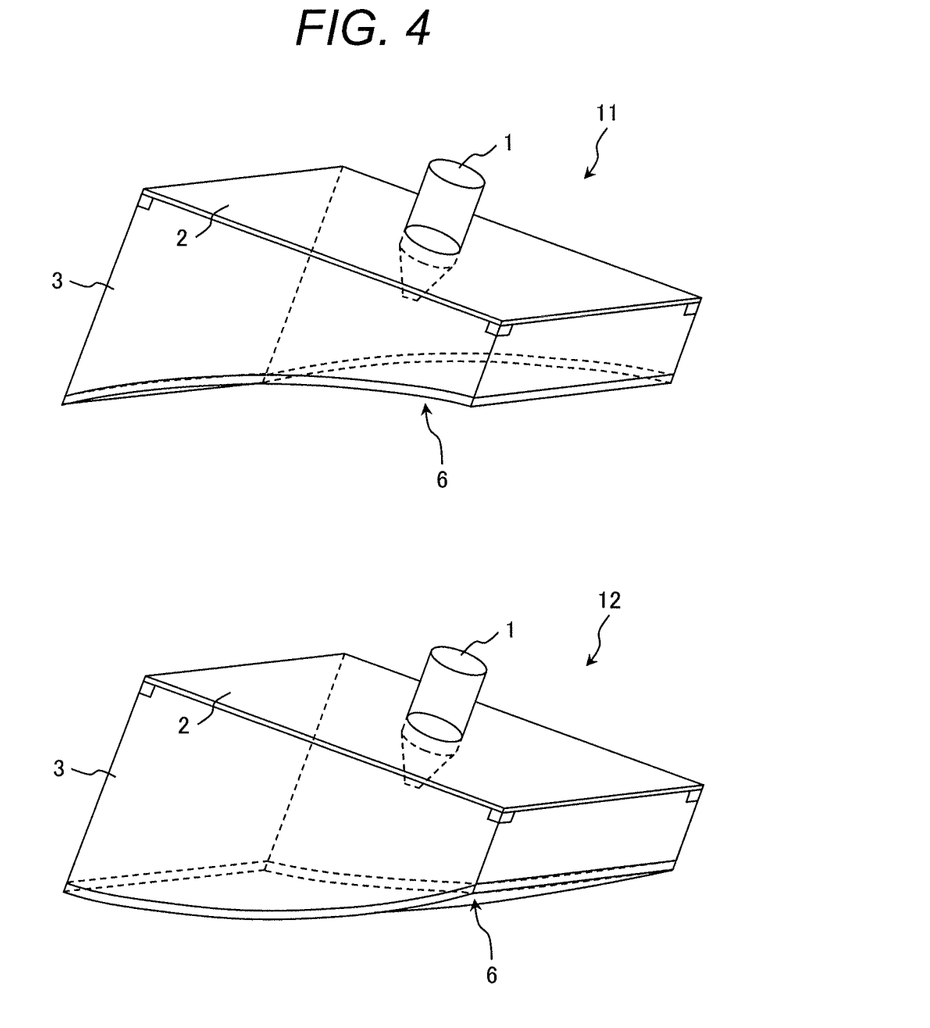
FIG. 4 is a schematic illustration showing perspective views of another embodiment of an X-ray diffraction instrument according to the present invention.

FIG. 4 is a schematic illustration showing perspective views of another embodiment of an X-ray diffraction instrument according to the present invention. In the X-ray diffraction instruments 11 and 12 illustrated in FIG. 4, each lower end of the cylinder-like shields 3 (on the side of an unshown underlying measurement object, on the opposite side of the X-ray detector) is shaped so as to conform to a surface contour of the underlying measurement object. By this configuration, the X-ray diffraction measurement can be performed also for objects having a curved surface (such as outer surfaces of large diameter pipes and inner surfaces of pressure vessels) for which X-ray diffraction measurement has previously been difficult. The cylinder-like shield 3 is preferably made of a plastic material because of good formability and light weight.

The X-ray diffraction instruments 11 and 12 further include, as another type of standard powder attachment device, a polymer sheet 6 having an X-ray measurement standard powder dispersed therein. The polymer sheet 6 covers the open end of the cylinder-like shield 3 facing the measurement object. Before an X-ray diffraction measurement, the polymer sheet 6 of the cylinder-like shield 3 is pushed against the surface of the measurement object, thereby bringing the polymer sheet 6 into close contact with the surface of the measurement object. The polymer sheet 6 will never scatter the standard powder. Therefore, the polymer sheet 6 is particularly advantageously used in X-ray measurement environments where contamination by foreign materials is unacceptable. Needless to say, the X-ray diffraction instrument 10 as shown in FIG. 1 may be equipped with the polymer sheet 6 instead of the injector 4. Also, the X-ray diffraction instruments 11 and 12 may be equipped with the injector 4 instead of the polymer sheet 6.

The polymer used for the polymer sheet 6 is not particularly limited so long as the polymer sheet 6 does not attenuate X-ray and is sufficiently flexible so as to conform to the underlying surface of the measurement object. For example, silicone rubber may be used. A thickness of the polymer sheet 6 is preferably from 0.1 to 0.5 mm. A polymer sheet 6 of less than 0.1 mm in thickness is prone to tear easily. On the other hand, a polymer sheet 6 of more than 0.5 mm in thickness cannot sufficiently conform to the underlying measurement object.

Figure 5:
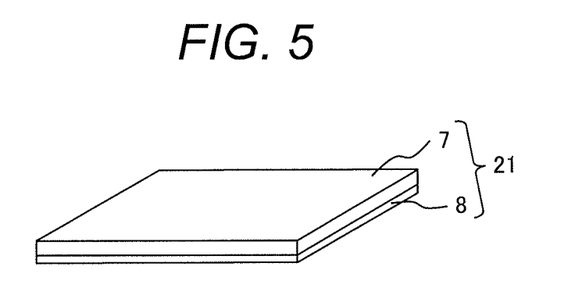
FIG. 5 is a schematic illustration showing a perspective view of an imaging plate as an example of a two-dimensional X-ray detector used in the invented X-ray diffraction instrument.

FIG. 5 is a schematic illustration showing a perspective view of an imaging plate as an example of a two-dimensional X-ray detector used in the invented X-ray diffraction instrument. As illustrated in FIG. 5, an imaging plate 21 includes; a support plate 7 made of a plastic or the like; and an X-ray receiving layer 8 made of a photostimulable phosphor (BaFX: $Eu^{2+}$, X=Br, I) formed on the support plate 7. The imaging plate 21 is illustrated as being rectangular in FIG. 5, but any other shape is also possible.

The BaFX:$Eu^{2+}$ (X=Br, I) photostimulable phosphor has a wide dynamic range and high sensitivity to a wide variety of ionizing radiations. It also has a high spatial resolution. In addition, it can be formed into large shapes, thus enabling large area two-dimensional X-ray detection. When the BaFX: $Eu^{2+}$ (X=Br, I) photostimulable phosphor is irradiated with an ionizing radiation beam, electron-hole pairs are generated in the phosphor crystal and the electrons are trapped by photostimulable phosphor. The amount of the trapped electrons is proportional to the irradiation amount.

When the photostimulable phosphor is irradiated with an excitation light (such as He—Ne (helium-neon) laser), the radiation energy stored in the phosphor will be released as a photostimulated luminescence. This mechanism is utilized in the imaging plate 21 as follows: After the imaging plate 21 is irradiated with an X-ray diffraction pattern, the phosphor on the imaging plate 21 is photostimulated by scanning a laser beam two-dimensionally across the surface of the imaging plate 21. Then, the resulting photostimulated luminescence signals are sequentially detected with a photomultiplier tube (PMT) or the like and recorded as a time series signal. In this manner, the intensity distribution of the X-ray diffraction pattern recorded can be read out.

The radiation energy stored in the photostimulable phosphors can be removed by exposure to visible light. Therefore, the imaging plate 21 using a photostimulable phosphor can be repeatedly used. In other words, in order to prevent destruction of an X-ray diffraction pattern stored on the imaging plate 21, the imaging plate 21 is preferably prevented from exposure to visible light during the X-ray diffraction measurement. For example, the cylinder-like shield 3 preferably shields the imaging plate 21 from both X-ray and visible light. Alternatively, the imaging plate 21 may be housed in a cartridge that transmits X-ray but blocks visible light. In this case, the cylinder-like shield 3 does not necessarily block visible light. Preferably, the imaging plate 21 is detachable and easily exchangeable in view of operability and usability of the X-ray diffraction instruments 10 to 12.

Figure 6:
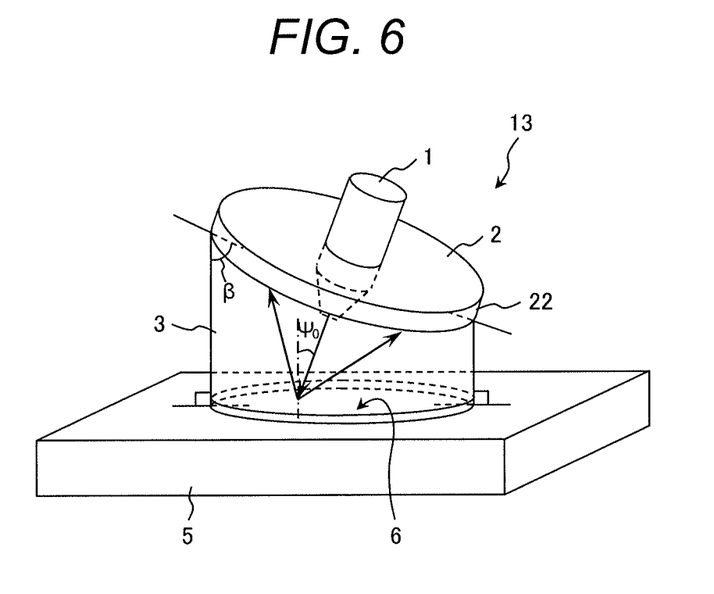
FIG. 6 is a schematic illustration showing a perspective view of still another embodiment of an X-ray diffraction instrument according to the present invention.

FIG. 6 is a schematic illustration showing a perspective view of still another embodiment of an X-ray diffraction instrument according to the present invention. As illustrated in FIG. 6, the X-ray diffraction instrument 13 of this embodiment employs a two-dimensional position sensitive proportional counter 22 as the plate-like X-ray detector 2. The use of the position-sensitive proportional counter 22 enables simultaneous measurement and recording (imaging) of an X-ray diffraction pattern. FIG. 6 illustrates an exemplary configuration in which: the polymer sheet 6 is used as a standard powder attachment device; and the integral assembly of the counter 22 and the X-ray emitter 1 is attached obliquely (90°−β) to the upper end of the cylinder-like shield 3 (on the side of the counter 22) so that the emitted X-ray beam impinges on the surface of the measurement object 5 at an incident angle Ψ.

As has been described, in the invented X-ray diffraction instrument, a two-dimensional plate-like X-ray detector and an X-ray emitter are integrally fixed to each other, which are together attached to a cylinder-like shield. The cylinder-like shield works to define an orientation of the X-ray emitter. Thus, the invented X-ray diffraction instrument does not require any actuator for adjusting the orientation of the X-ray emitter, and thus can be made smaller and lighter than conventional X-ray diffraction instruments.

In addition, the cylinder-like shield works both to protect X-ray and to define the orientation of the X-ray emitter (see FIG. 3). It also works to adjust the invented X-ray diffraction instrument to a shape and a size of a measurement object (see FIG. 4). Thus, there is no particular limitation on the shape and size of objects measurable by the invented X-ray diffraction instrument.

Moreover, the X-ray diffraction instrument of the present invention is equipped with an injector to inject a dispersion of a standard powder for X-ray measurement or a polymer sheet having an X-ray measurement standard powder dispersed therein. This configuration enables the X-ray measurement standard powder to be stably attached to surfaces of the measurement objects. Therefore, accurate X-ray measurement can be performed irrespective of the orientation of the measurement surface. Hence, the X-ray diffraction instrument of the present invention can be particularly advantageously used for large and/or stationary measurement objects that should not or cannot be moved, tilted, rotated, etc.

The above described imaging plate and position-sensitive proportional counter used as the two-dimensional X-ray detector can both achieve the above-described advantages of the invention. Imaging plates have the advantages of simple structure and low cost. In addition, they can be easily formed to a desire shape and size so as to be suited to an object to be measured. On the other hand, two-dimensional position sensitive proportional counters have disadvantages of a complicated structure and high cost compared to imaging plates, but have advantages of being able to simultaneously provide both a high precision X-ray diffraction measurement and the recording (imaging) of the measurement result. The choice between these two types is made depending on the application.

EXAMPLES

As already described, large apparatuses (such as pressure vessels) in plants or other systems must be cheeked for the safety against stress corrosion cracking. For example, the residual stresses in inner surfaces of the pressure vessel walls sometimes need to be measured and evaluated by X-ray diffraction techniques. In such measurements, measurement surfaces may often be vertical or face downward. The present invention can be advantageously used in such measurement environments. The present invention will be described more specifically below by way of an example. However, the present invention is not limited to the specific example below.

Figure 7:
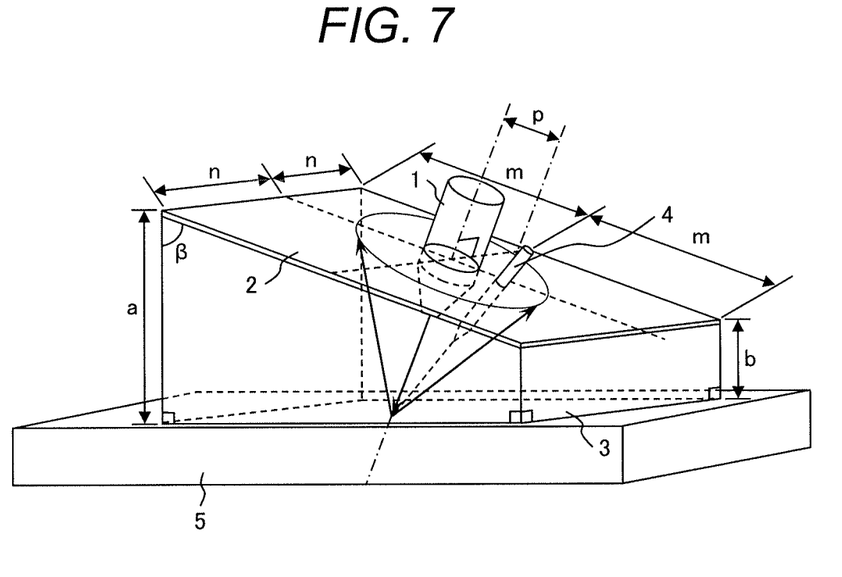
FIG. 7 is a schematic illustration showing a perspective view of a preferred example of the X-ray diffraction instrument according to the present invention.

FIG. 7 is a schematic illustration showing a perspective view of a preferred example of the X-ray diffraction instrument according to the present invention, where a=30 mm, b=10 mm, m=20 mm, n=25 mm, p=8 mm, and β=60°. An X-ray emitter 1 was integrally secured to a two-dimensional X-ray detector 2 in such a manner as to perpendicularly penetrate through a central portion of the X-ray detector 2. The X-ray detector 2 was attached to a cylinder-like shield 3 in such a manner that the perimeter of the upper end of the cylinder-like shield 3 abutted the perimeter of the X-ray detector 2. An injector 4 was integrally extended through the X-ray detector 2 and was oriented in such a manner that it could inject a standard powder dispersion onto an X-ray measurement area of a measurement object 5. An imaging plate was used as the two-dimensional X-ray detector 2 and an Mn (manganese) target X-ray tube was used as the X-ray emitter 1.

A test plate (1000 mm×500 mm×20 mm) of a stainless steel (JIS SUS304) was used as the measurement object 5. In order to simulate an actual inner surface of a pressure vessel wall, the test plate was machined in such a manner that tensile residual stresses were induced in one of its broad surfaces. The test plate was placed in such a manner that its longitudinal direction was perpendicular to the ground and the machined surface was the measurement surface.

Figure 8A:
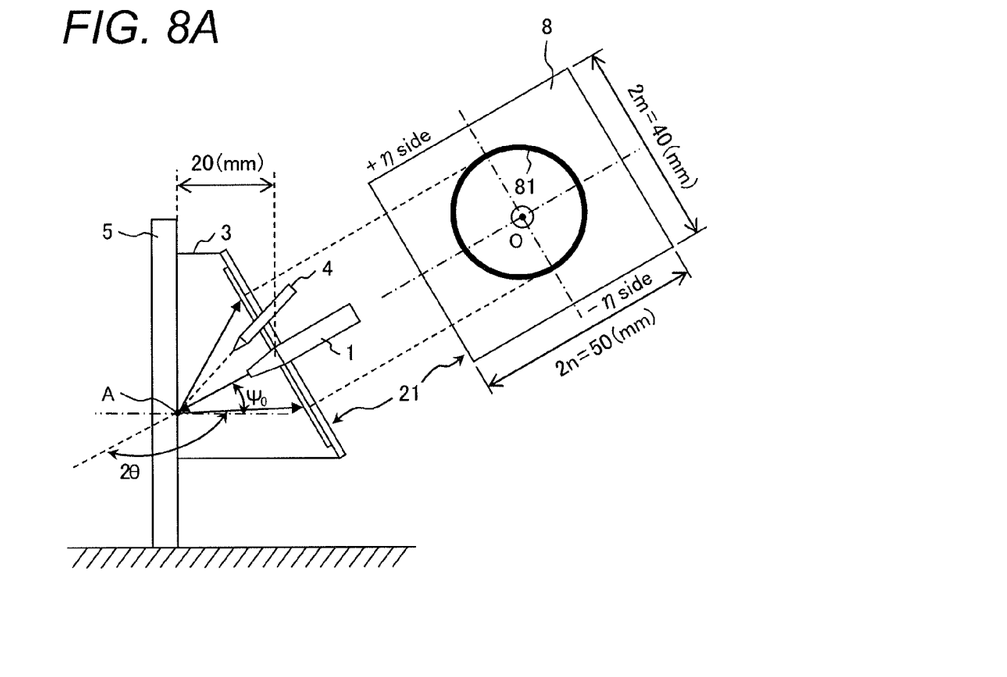
FIG. 8A is a schematic illustration showing a side view of the X-ray diffraction measurement of a measurement object by means of the X-ray diffraction instrument of the present invention.

FIG. 8A is a schematic illustration showing a side view of the X-ray diffraction measurement of a measurement object by means of the X-ray diffraction instrument of the present invention; and FIG. 8B is a schematic illustration showing a side view of the X-ray diffraction measurement of a standard powder provided at the measurement point by means of the same X-ray diffraction instrument. As shown in FIG. 8A, first, the X-ray diffraction instrument of FIG. 7 was pushed against the vertical measurement surface of the measurement object 5. The resulting distance between the center of the imaging plate 21 and the measurement surface was approximately 20 mm, and the resulting X-ray incident angle $\Psi_0$ (between the measurement surface normal and the axis of the X-ray emitter 1) was 30°. An X-ray diffraction measurement was performed by irradiating the measurement point A with Mn—Kα line (wavelength: $2.10314 \times 10^{-10}$ m) for 5 to 10 min. The X-ray incident on the measurement point A was diffracted at a diffraction angle θ and captured on the receiving surface 8 of the imaging plate 21 as an X-ray diffraction ring (Debye ring) 81 of the measurement point A.

Figure 8B:
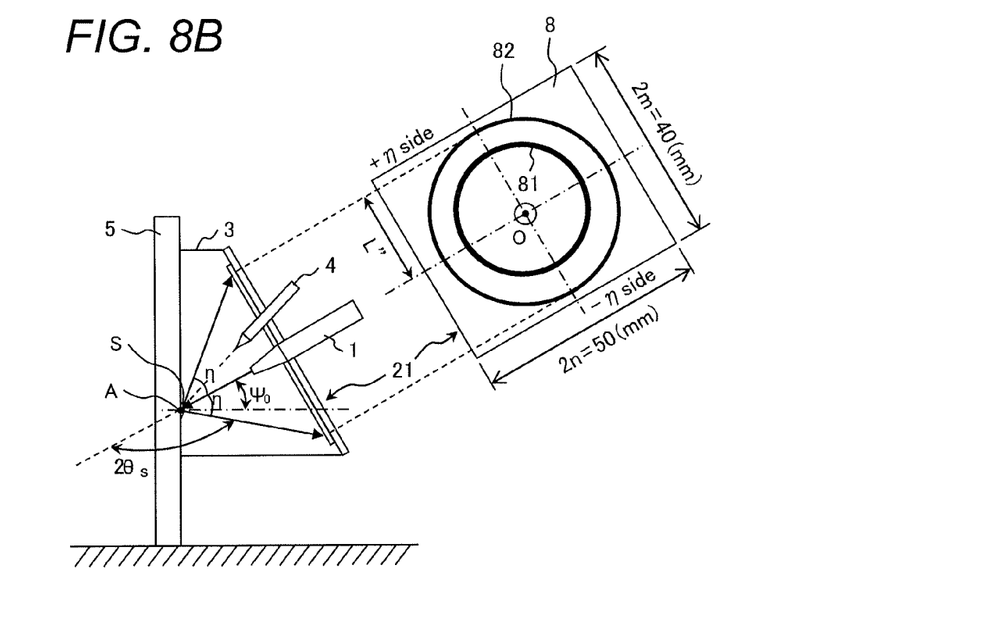
FIG. 8B is a schematic illustration showing a side view of the X-ray diffraction measurement of a standard powder provided at the measurement point by means of the X-ray diffraction instrument of the present invention.

Next, as shown in FIG. 8B, a dispersion of a standard powder was injected from the injector 4 onto the measurement point A, thereby forming a standard powder coating S. A pure copper powder whose internal strain was sufficiently relaxed was used as the standard powder. Then, an X-ray diffraction measurement was performed by irradiating the standard powder coating S with Mn—Kα line for 5 to 10 min. The X-ray incident on the standard powder coating S was diffracted at a diffraction angle $\theta_s$ and captured on the receiving surface 8 of the imaging plate 21 as an X-ray diffraction ring (Debye ring) 82 of the standard powder. After this measurement, the standard powder coating S was completely wiped off with a wet cloth.

Figure 9:
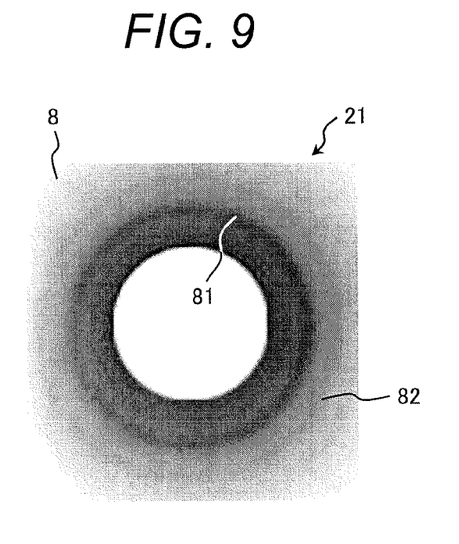
FIG. 9 shows an example of a visualization of the X-ray diffraction rings from a measurement point and a standard powder.

In order to accurately evaluate the residual stress at the measurement point A by using the imaging plate 21, the diffraction angle θ of the X-ray diffraction ring 81 from the measurement point A needs to be accurately estimated. Furthermore, in order to accurately estimate the diffraction angle θ, the X-ray diffraction ring 82 from the standard powder needs to be accurately recorded. FIG. 9 shows an example of a visualization of the X-ray diffraction rings from a measurement point and a standard powder. As can be seen, the X-ray diffraction ring 81 from the measurement point A and the X-ray diffraction ring 82 from the standard powder were clearly recorded on the receiving surface 8 of the imaging plate 21.

The residual stress at the measurement point A can be estimated by cos α method, a residual stress estimation method based on elastic theory. As illustrated in FIGS. 8(a) and 8(b), η is an angle between the incident X-ray beam and a diffracted X-ray beam. The "+η side" is defined as the side where the distance between any irradiated position and measurement surface is less than the distance between the center O of the imaging plate 21 and the measurement surface, and the "−η side" is defined as the side where the distance between any irradiated position and measurement surface is greater than the distance between the center O of the imaging plate 21 and the measurement surface. $\theta_0$ is the theoretical value of diffraction angle from a measurement object 5 having no strain, and $\theta_s$ is the theoretical value of diffraction angle from the standard powder.

Figure 10:
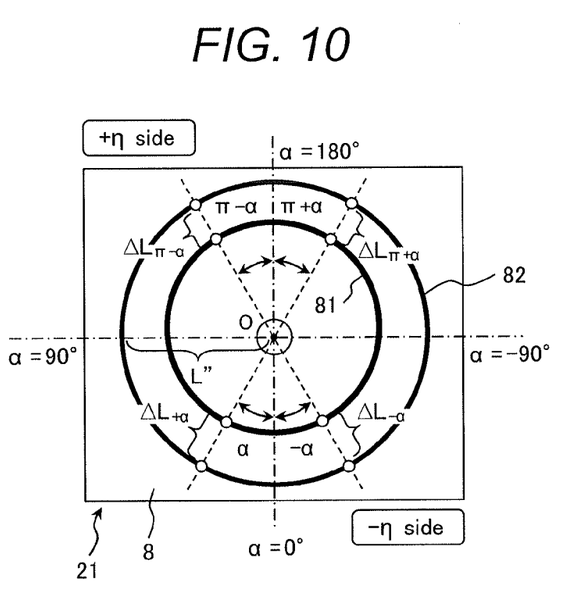
FIG. 10 is a schematic illustration showing an X-ray diffraction ring for explaining parameters required for the cos α method calculation.

FIG. 10 is a schematic illustration showing an X-ray diffraction ring for explaining parameters required for the cos α method calculation. First, at plural points along the entire X-ray diffraction ring 81, the peak intensity position of the X-ray intensity profile in the radial direction (the ring width direction) is determined by a method of full-width at half maximum. By using these data, the most approximate circle for the X-ray diffraction ring 81 (hereinafter, the "approximate circle 81") is determined by a least squares method. The same procedure is made for the X-ray diffraction ring 82 to determine the approximate circle for the ring 82 (hereinafter, the "approximate circle 82"). Then, the center O (corresponding to the X-ray incident point, i.e. the measurement point A) and the radius L" of the approximate circle 82 are determined.

Next, as illustrated in FIG. 10, the difference ΔL between the radius of the approximate circle 82 and the radius of the approximate circle 81 is measured at predefined central angles of the approximate circle 82. The predefined central angles are "+α", "−α", "π+α" and "π−α", where α is from 5° to 80° with an increment of 5°. The corresponding radius differences ΔLs are represented by "$\Delta L_{+\alpha}$", "$\Delta L_{-\alpha}$", "$\Delta L_{\pi+\alpha}$", and "$\Delta L_{\pi-\alpha}$". Herein, the above central angle α on the approximate circle 81 is measured clockwise, where 0 (deg) is defined as the position with the greatest distance to measurement surface (the bottom point on the approximate circle 82 in FIG. 10).

The residual stress $\sigma_x$ at the measurement point A can be calculated from Equations (1) to (4) below.

$$L_\alpha = [(\Delta L_{+\alpha} - \Delta L_{\pi+\alpha}) + (\Delta L_{-\alpha} - \Delta L_{\pi-\alpha})] \quad \text{Eq. (1)}$$

$$M_\alpha = L_\alpha / \cos \alpha \quad \text{Eq. (2)}$$

$$K_\alpha = (\cos^2 2\theta_0 \tan 2\theta_s / 2L'' \tan \theta_0) \cdot E_{hkl}/(1+\upsilon_{hkl}) \quad \text{Eq. (3)}$$

$$\sigma_x = K_\alpha M_\alpha / \{\sin^2(\psi_0 - \eta) - \sin^2(\psi_0 + \eta)\} \quad \text{Eq. (4)}$$

For each α, $L_\alpha$ is calculated by substituting $\Delta L_{+\alpha}$, $\Delta L_{-\alpha}$, $\Delta L_{\pi+\alpha}$ and $\Delta L_{\pi-\alpha}$ into Eq. (1), and the $L_\alpha$ values are plotted against the cos α values. Then, the gradient $M_\alpha$ of this $L_\alpha$–cos α plot is determined by a least squares method (see Eq. (2)). Next, $K_\alpha$ is calculated from Eq. (3).

In Eq. (3), "$E_{hkl}/(1+\upsilon_{hkl})$" is the X-ray diffraction elastic constant for the (hkl) diffraction plane of the measurement object 5. In this example, stainless steel (JIS SUS304) was used as the measurement object 5, and its (311) plane was used as the (hkl) diffraction plane. However, in this example, typical well-known values for JIS SUS304 (the Young's modulus E=200 GPa and the Poisson's ratio υ=0.3) were used to calculate $K_\alpha$ for the sake of convenience. As can be seen from Eq. (3), $K_\alpha$ can be calculated from material constants, and is therefore a constant independent of the residual stress.

The residual stress $\sigma_x$ at the measurement point A can be obtained by substituting these parameter values into Eq. (4). Using the method described above, the residual stress was estimated at several positions on the machined surface of the measurement object 5. The result showed that the machined surface of the test plate had tensile residual stresses of 200 to 300 MPa. The above results demonstrate that the X-ray diffraction instrument according to the present invention can perform accurate X-ray diffraction measurement without any particular limitation on the size or shape of the measurement object or the orientation of the measurement surface.

In the above example, after the "X-ray diffraction measurement of the measurement object", the "formation of the standard powder coating" and the "X-ray diffraction measurement of the standard powder" were performed. However, the present invention is not limited to such a procedure. When the standard powder coating can transmit X-ray sufficiently so that the diffracted X-ray from the underlying measurement object has sufficient intensity, the "X-ray diffraction measurement of the measurement object" and the "X-ray diffraction measurement of the standard powder" may be conducted simultaneously after the "formation of the standard powder coating". If a polymer sheet having a standard powder dispersed therein is used, the "X-ray diffraction measurement of a measurement object" and the "X-ray diffraction measurement of the standard powder" will be conducted simultaneously by necessity.

Although the present invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. An X-ray diffraction instrument for performing an X-ray diffraction measurement to an object larger than an X-ray detector thereof, comprising:
    a two-dimensional plate-like X-ray detector;
    an X-ray emitter integrated with the X-ray detector so as to penetrate the plate of the X-ray detector;
    a cylinder-like shield to define an orientation of the X-ray emitter and to prevent X-ray leakage, the X-ray detector being attached to one open end of the cylinder-like shield; and
    a standard powder attachment device to attach a standard powder for X-ray diffraction measurement to a surface of an object to be measured.

2. The X-ray diffraction instrument according to claim 1, wherein:
    the standard powder attachment device is an injector to inject a dispersion of the standard powder in a dispersion medium; and
    the injector is integrated with the X-ray detector so as to penetrate the X-ray detector.

3. The X-ray diffraction instrument according to claim 1, wherein the standard powder attachment device is a polymer sheet having the standard powder dispersed therein; and the polymer sheet covers the other open end of the cylinder-like shield facing a surface of the object to be measured, and
    wherein the polymer sheet is attached to the object surface by pushing the polymer sheet against the object surface to be measured.

4. The X-ray diffraction instrument according to claim 3, wherein a thickness of the polymer sheet is from 0.1 to 0.5 mm.

5. The X-ray diffraction instrument according to claim 1, wherein the cylinder-like shield is detachable and easily exchangeable for another cylinder-like shield.

6. The X-ray diffraction instrument according to claim 2, wherein the cylinder-like shield is detachable and easily exchangeable for another cylinder-like shield.

7. The X-ray diffraction instrument according to claim 1, wherein the X-ray emitter includes a sighting device.

8. The X-ray diffraction instrument according to claim 2, wherein the X-ray emitter includes a sighting device.

9. The X-ray diffraction instrument according to claim 1, wherein the X-ray detector is an imaging plate including a photostimulable phosphor layer.

10. The X-ray diffraction instrument according to claim 2, wherein the X-ray detector is an imaging plate including a photostimulable phosphor layer.

11. The X-ray diffraction instrument according to claim 9, wherein the cylinder-like shield blocks visible light.

12. The X-ray diffraction instrument according to claim 9, wherein the imaging plate is housed in a cartridge that transmits X-ray but blocks visible light.

13. The X-ray diffraction instrument according to claim 9, wherein the imaging plate is detachable and easily exchangeable for another imaging plate.

14. The X-ray diffraction instrument according to claim 1, wherein the X-ray detector is a position-sensitive proportional counter.

15. The X-ray diffraction instrument according to claim 2, wherein the X-ray detector is a position-sensitive proportional counter.

* * * * *